United States Patent
Breton et al.

(10) Patent No.: US 7,651,680 B2
(45) Date of Patent: Jan. 26, 2010

(54) METHODS AND COMPOSITIONS FOR PREVENTING AND TREATING SENSITIVE AND DRY SKIN

(75) Inventors: Lionel Breton, Versailles (FR); Roland Jourdain, Meudon la Foret (FR); Audrey Gueniche, Malmaison (FR); Isabelle Bureau-Franz, Morges (CH); Stephanie Blum-Sperisen, Mont-Pelerin (CH)

(73) Assignees: L'Oreal, Paris (FR); Nestec S.A., Vevey (CH)

( * ) Notice: Subject to any disclaimer, the term of this patent is extended or adjusted under 35 U.S.C. 154(b) by 0 days.

(21) Appl. No.: 11/159,198

(22) Filed: Jun. 23, 2005

(65) Prior Publication Data

US 2006/0008453 A1  Jan. 12, 2006

Related U.S. Application Data

(60) Provisional application No. 60/623,039, filed on Oct. 29, 2004.

(30) Foreign Application Priority Data

Jun. 23, 2004  (FR)  .................. 04 51317

(51) Int. Cl.
A61K 33/00 (2006.01)
A61K 35/74 (2006.01)

(52) U.S. Cl. .................. 424/78.02; 424/93.1; 424/93.4; 424/93.51; 424/600

(58) Field of Classification Search .............. 424/78.02, 424/93.1, 93.4, 93.51, 600
See application file for complete search history.

(56) References Cited

U.S. PATENT DOCUMENTS

| | | | | | |
|---|---|---|---|---|---|
| 3,156,355 | A | * | 11/1964 | Rodgers | 206/459.5 |
| 5,614,209 | A | * | 3/1997 | Ford | 424/443 |
| 6,461,627 | B1 | * | 10/2002 | Ichioka et al. | 424/401 |
| 6,506,413 | B1 | * | 1/2003 | Ramaekers | 424/535 |
| 2003/0003107 | A1 | | 1/2003 | Farmer | |
| 2004/0001817 | A1 | | 1/2004 | Giampapa | |
| 2006/0018986 | A1 | | 1/2006 | Breton | |

FOREIGN PATENT DOCUMENTS

| | | |
|---|---|---|
| DE | 202 02 562 | 6/2002 |
| EP | 0 110 550 A1 | 6/1984 |
| EP | 0 399 909 A1 | 11/1990 |
| EP | 0 737 471 A2 | 10/1996 |
| EP | 0 806 933 B1 | 11/1997 |
| EP | 0 904 784 | 3/1999 |
| EP | 0 931 543 A1 | 7/1999 |
| EP | 1 110 555 A1 | 6/2001 |
| EP | 1 169 925 A1 | 1/2002 |
| EP | 1 236 463 A1 | 9/2002 |
| EP | 1 364 586 A1 | 11/2003 |
| EP | 1 374 913 A1 | 1/2004 |
| FR | 2 848 448 | 6/2004 |
| FR | 2 851 889 | 9/2004 |
| RU | 2 228 184 C2 | 5/2004 |
| WO | WO 99/49877 | 10/1999 |
| WO | WO 00/49885 | 8/2000 |
| WO | WO 00/70972 A1 | 11/2000 |
| WO | WO 01/15715 A2 | 3/2001 |
| WO | WO 01/17365 A1 | 3/2001 |
| WO | WO 02/28402 A1 | 4/2002 |
| WO | WO 03/071883 A1 | 9/2003 |
| WO | WO 2004/112509 | 12/2004 |

* cited by examiner

Primary Examiner—Ruth A Davis
(74) Attorney, Agent, or Firm—Oliff & Berridge, PLC

(57) ABSTRACT

Compositions for preventing and/or treating sensitive and/or dry skin include at least an effective amount of at least one agent and at least an effective amount of at least one divalent inorganic cation, wherein the at least one agent includes at least one member selected from the group consisting of at least one microorganism, a fraction of the at least one microorganism and a metabolite of the at least one microorganism. Methods for preparing such compositions and cosmetic treatment methods employing such compositions are also provided.

23 Claims, No Drawings

METHODS AND COMPOSITIONS FOR PREVENTING AND TREATING SENSITIVE AND DRY SKIN

CROSS-REFERENCE TO RELATED APPLICATIONS

This application claims the benefit of French Application No. 04 51317, filed on Jun. 23, 2004, and U.S. Provisional Application No. 60/623,039, filed on Oct. 29, 2004, the entire disclosures of which are incorporated by reference herein.

BACKGROUND

The present invention includes cosmetic treatment methods and compositions, such as cosmetic and/or dermatological compositions, for preventing and/or treating sensitive and/or dry skin.

In general, sensitive skin is defined by a specific reactivity of the skin. However, as opposed to skin described as allergic, this reactivity is not the result of an immunological process, i.e., it does not occur only in skin that is already sensitized, in response to the presence of an allergen. Its mechanism is said to be aspecific.

This skin reactivity generally results in the manifestation of signs of discomfort in response to the subject coming into contact with a triggering element that may have various origins. It may involve the application of a cosmetic product at the surface of the sensitive skin, food intake or exposure to abrupt temperature variations, atmospheric pollution and/or ultraviolet or infrared rays. Associated factors such as age and the type of skin also exist. Sensitive skin is more common in dry or oily skin than in normal skin.

The appearance of these signs of discomfort, which appear within minutes after the individual has come into contact with the triggering element, is one of the essential characteristics of sensitive skin. These signs are essentially dysaesthetic sensations. The term "dysaesthetic sensations" is intended to encompass more or less painful sensations experienced in a region of skin, such as stinging, tingling, itching or pruritus, burning, heating, discomfort, tautness, etc. These subjective signs most commonly exist in the absence of visible chemical signs such as redness and desquamations. At this time, it is known that these skin irritation and intolerance reactions are associated with a release of neuropeptides by the nerve endings in the epidermis and the dermis.

EP 737 471 discloses that incorporation of certain alkaline earth metal salts into a cosmetic and/or dermatological composition makes it possible to effectively oppose the release of these neuropeptides and to advantageously obtain a preventive and/or curative effect for sensitive skin. EP 806 933 illustrates the effectiveness of strontium salts for treating irritable skin.

However, there presently is no completely satisfactory solution available for preventing and/or treating sensitive skin, and this problem is particularly exacerbated when the sensitive skin is dry skin. Dry skin manifests itself through a sensation of tautness and/or of tension and it is often associated with a decrease in the level of moisture of the skin and an impairment of barrier function, measured through an imperceptible loss of water.

WO 02/28402 describes that probiotic microorganisms can have a beneficial effect in the regulation of skin hypersensitivity reactions such as inflammatory and allergic reactions that are the result of an immunological process as opposed to the reactivity of sensitive skin. "Probiotics in the management of atopic eczema," Clinical and Experimental Allergy 2000, Volume 30, pages 1604-1610, describes the effect of probiotics on immune mechanisms in infants, for instance atopic dermatitis.

EP 110 550 describes using bacterial agents, such as probiotics, for stabilizing and/or regulating skin ecoflora. These compounds are described as being effective for preventing the adhesion of pathogenic flora to the skin.

SUMMARY

Unexpectedly, the present inventors discovered that microorganisms, such as probiotic microorganisms, can be effective, particularly in adults, for treating sensitive skin, particularly sensitivity associated with dry skin, when combined with an effective amount of at least one divalent inorganic cation, such as an alkaline earth metal salt.

This effectiveness is particularly unexpected because these two types of active agents were, until now, presumed to act via two completely different mechanisms involving different methods of administration, i.e., mainly oral administration for the microorganisms and mainly topical administration for the divalent inorganic cations. Further, the effectiveness of these agents in treating sensitivity associated with dry skin is completely unexpected.

Exemplary cosmetic treatment methods for preventing and/or treating sensitive and/or dry skin according to the present invention include orally administering a composition comprising at least an effective amount of at least one agent and at least an effective amount of at least one divalent inorganic cation. In various exemplary embodiments, the at least one agent comprises at least one member selected from the group consisting of at least one microorganism, a fraction of the at least one microorganism and a metabolite of the at least one microorganism.

Exemplary cosmetic treatment methods for preventing and/or treating sensitive and/or dry skin according to the present invention include orally or topically administering a composition comprising at least an effective amount of at least one agent and at least an effective amount of at least one divalent inorganic cation. In various exemplary embodiments, the at least one agent comprises at least one member selected from the group consisting of at least one microorganism, a fraction of the at least one microorganism and a metabolite of the at least one microorganism, and the at least one divalent inorganic cation is in the form of a salt other than a sulfate.

Exemplary methods for preparing compositions for oral administration for preventing and/or treating sensitive and/or dry skin according to the present invention include combining at least an effective amount of at least one agent and at least an effective amount of at least one divalent inorganic cation. In various exemplary embodiments, the at least one agent comprises at least one member selected from the group consisting of at least one microorganism, a fraction of the at least one microorganism and a metabolite of the at least one microorganism.

Exemplary methods for preparing compositions for preventing and/or treating sensitive and/or dry skin according to the present invention include combining at least an effective amount of at least one agent and at least an effective amount of at least one divalent inorganic cation. In various exemplary embodiments, the at least one agent comprises at least one member selected from the group consisting of at least one microorganism, a fraction of the at least one microorganism and a metabolite of the at least one microorganism, and the at least one divalent inorganic cation is in the form of a salt other than a sulfate.

Exemplary cosmetic and/or dermatological compositions for preventing and/or treating sensitive and/or dry skin according to the present invention include at least an effective amount of an agent and at least an effective amount of at least two alkaline earth metals in a physiologically acceptable carrier. In various exemplary embodiments, the at least one agent comprises at least one member selected from the group consisting of at least one microorganism, a fraction of the at least one microorganism and a metabolite of the at least one microorganism, and each of the at least two alkaline earth metals is in the form of an anhydrous organic salt, a hydrated organic salt or a chelated complex.

Exemplary cosmetic and/or dermatological compositions for preventing and/or treating sensitive and/or dry skin according to the present invention include at least an effective amount of at least one agent and at least an effective amount of at least one alkaline earth metal in a physiologically acceptable carrier. In various exemplary embodiments, the at least one agent comprises at least one member selected from the group consisting of at least one microorganism, a fraction of the at least one microorganism and a metabolite of the at least one microorganism, and the at least one alkaline earth metal is in the form of a salt selected from the group consisting of a bicarbonate, a glycerophosphate, a nitrate, an acetate, a hydroxide, an α-hydroxy acid salt, a salt of a fruit acid, an amino acid salt and a fatty acid salt.

DETAILED DESCRIPTION OF EMBODIMENTS

Exemplary embodiments of methods of cosmetic treatment for preventing and/or treating sensitive and/or dry skin include the oral administration of at least an effective amount of at least one microorganism, in particular a probiotic microorganism, and/or a fraction thereof and/or a metabolite thereof, in combination with an effective amount of at least one divalent inorganic cation.

Exemplary methods include the oral or topical administration of at least an effective amount of at least one microorganism, in particular a probiotic microorganism, and/or a fraction thereof and/or a metabolite thereof, in combination with an effective amount of at least one divalent inorganic cation in the form of a salt other than a sulfate.

Exemplary embodiments of the present invention include the use of an effective amount of at least one microorganism, in particular a probiotic microorganism, and/or a fraction thereof and/or a metabolite thereof, in combination with an effective amount of at least one divalent inorganic cation, for preparing compositions intended for oral administration and useful for preventing and/or treating sensitive and/or dry skin.

Exemplary compositions are formulated in the form of food supplements, or even foodstuffs.

Further exemplary compositions are in the form of cosmetic and/or dermatological compositions.

In exemplary embodiments, compositions including at least an effective amount of at least one microorganism, in particular a probiotic microorganism, and/or a fraction thereof and/or a metabolite thereof, in combination with an effective amount of at least one divalent inorganic cation in the form of a salt other than a sulfate are used to prevent and/or treat sensitive and/or dry skin.

In exemplary embodiments, cosmetic and/or dermatological compositions that are particularly useful for preventing and/or treating sensitive and/or dry skin include at least an effective amount of at least one microorganism, in particular a probiotic microorganism, and/or a fraction thereof and/or a metabolite thereof, in combination with an effective amount of at least two alkaline earth metals in the form of anhydrous organic salts, hydrated organic salts, or chelated complexes, in a physiologically acceptable carrier.

Further exemplary cosmetic and/or dermatological compositions that are useful for preventing and/or treating sensitive and/or dry skin include at least an effective amount of at least one microorganism, in particular probiotic microorganism, and/or a fraction thereof and/or a metabolite thereof, in combination with an effective amount of at least one alkaline earth metal in the form of a salt chosen from bicarbonates, glycerophosphates, nitrates, acetates, hydroxides, α-hydroxy acid salts, such as citrates, tartrates, lactates and malates, or salts of fruit acids, amino acid salts, such as aspartates, arginates and fumarates, or fatty acid salts such as palmitates, oleates, caseinates and behenates, in a physiologically acceptable carrier.

Sensitive and/or Dry Skin

As specified above, sensitive skin is different from allergic skin. Its reactivity is not the result of an immunological process and generally only results in dysaesthetic sensations.

For obvious reasons, a lack of visible symptoms makes it difficult to diagnose sensitive skin. Most commonly, diagnosis is based on the results of questioning a patient. Such symptomology makes it possible to differentiate between sensitive skin possibly associated with dry skin, and contact irritation or allergy for which, on the other hand, visible inflammatory signs exist.

Consequently, the development of "sensitive skin" products has required the provision of tools for evaluating the sensory reaction of the skin. The first tools were, right from their conception, inspired by the essential characteristic of sensitive skin, i.e., the presence of signs of discomfort induced by a topical application. Thus, the lactic acid "stinging test" was the first test proposed. It is carried out by recording the stinging sensations reported by a volunteer after application of a 10% lactic acid solution to the alar processes of the nose. Individuals who report moderate or strong stinging sensations are called "stingers" and are considered to have sensitive skin. Because of this skin sensitivity to topical product application, these individuals are then selected for testing "sensitive skin" products. More recently, in order to specifically activate the peripheral nerve endings involved in discomfort called nociceptors, which were recently identified as being involved in sensitive skin, new tests have been proposed that use other discomfort inducers such as capsaicin.

This second type of test, described in EP 1 374 913, is another particularly useful tool for diagnosing sensitive skin.

As used herein, the term "sensitive skin" encompasses irritable skin and intolerant skin.

Intolerant skin is skin that reacts to various factors, such as the application of cosmetic or dermatological products or soap, through sensations of heating, tautness, tingling and/or redness. In general, these signs are associated with erythema and hyperseborrhoeic or acneic skin, or even skin exhibiting rosacea with or without sores.

Irritable skin is skin which reacts through pruritus, i.e., through itching or prickling, to various factors such as the environment, emotions, foods, wind, rubbing, shaving, hard water with a high calcium concentration, temperature variations and/or wool.

In general, these two types of skin may be associated with dryness of the skin with or without sores or with skin that exhibits erythema.

As specified above, dryness of the skin is often associated with a decrease in the level of moisture of the skin, evaluated by corneometry, and with an impairment of the barrier function, measured through the imperceptible loss of water.

Dry skin essentially manifests itself through a sensation of tautness and/or tension. Dry skin is also rough to the touch and appears to be covered with scales. When the skin is slightly dry, these scales are abundant but not very visible to the naked eye. When this condition worsens, there are increasingly fewer of these scales but they are increasingly visible to the naked eye.

The cause of this dryness of the skin may be constitutional or acquired.

In the case of acquired dry skin, the involvement of outside parameters such as exposure to chemical agents, difficult climatic conditions or sunlight or alternatively certain therapeutic treatments (retinoids, for example) is determined. Under these outside influences, the skin can then become momentarily and locally dry. This can involve any type of normal and even oily skin.

In the case of constitutional dry skin, two categories can be distinguished: pathological skin and non-pathological skin.

Pathological constitutional dry skin is essentially represented by atopic dermatitis and ichthyoses. It is virtually independent of the outside conditions.

Atopic dermatitis is described as being associated with a deficiency in metabolism of the lipids of the stratum corneum, and in particular of the ceramides. This pathology presents itself in the form of more or less chronic xerosis concerning a large extent of the body, associated with inflammatory and pruriginous exacerbations in plaques.

Ichthyoses are pathologies characterized by a genetic deficiency that affects the keratinization process at various stages. It manifests itself through considerable desquamation in plaques.

Non-pathological constitutional dry skin is dry skin for which the severity can depend on the outside factors already mentioned. Senile skin (characterized by a general decrease in metabolism in the skin with age), fragile skin (very sensitive to outside factors and often accompanied by erythema and rosacea) and common xerosis (of probable genetic origin and manifesting itself predominantly on the face, the limbs and the back of the hands) enter into this skin category.

Exemplary compositions and methods according to this invention are particularly effective for preventing and/or treating sensitive and/or dry skin, and more particularly skin referred to as reactive, irritable and/or intolerant, acquired dry skin and/or constitutional dry skin.

Microorganisms and in Particular Probiotic Microorganisms

Microorganisms that are suitable for the invention include microorganisms that can be administered without risks to animals or humans.

In exemplary embodiments, at least one "probiotic-type" microorganism is used.

As used herein, the term "probiotic microorganism" is intended to encompass a living microorganism that, when consumed in an appropriate amount, has a positive effect on the health of its host (see "Joint FAO/WHO Expert Consultation on Evaluation of Health and Nutritional Properties of Probiotic in Food Including Powder Milk with Live Lactic Acid Bacteria, 6 Oct. 2001") and which can improve the intestinal microbial balance.

As used herein, the term "metabolite" encompasses any substance that is derived from the metabolism of microorganisms and that is also effective for treating sensitive skin.

As used herein, the term "fraction" encompasses a fragment of a microorganism that is effective for treating dry skin by analogy with said whole microorganism.

Exemplary microorganisms that are suitable for the invention include, but are not limited to, ascomycetes such as *Saccharomyces, Yarrowia, Kluyveromyces, Torulaspora, Schizosaccharomyces pombe, Debaromyces, Candida, Pichia, Aspergillus* and *Penicillium*, bacteria of the genus *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus* and *Lactobacillus* and mixtures thereof.

Exemplary ascomycetes that are particularly suitable for the present invention include, but are not limited to, *Yarrowia lipolitica* and *Kluyveromyces lactis*, along with *Saccharomyces cereviseae, Torulaspora, Schizosaccharomyces pombe, Candida* and *Pichia*.

Exemplary probiotic microorganisms include, but are not limited to:

Lactic bacteria such as:

*Lactobacillus* species: *acidophilus* (LC1, NCFB 1748); *amylovorus, casei* (Shirota), *rhamnosus* (strain GG), *brevis, crispatus, delbrueckii* (subsp *bulgaricus, lactis*), *fermentum, helveticus, gallinarum, gasseri, johnsonii, paracasei, plantarum, reuteri, rhamnosus* and *salivarius*;

Cocci: *Enterococcus* (*faecalis, faecium*), *Lactococcus lactis* (subspp *lactis* or *cremoris*), *Leuconstoc mesenteroides* subsp *dextranicum, Pediococcus acidilactici, Sporolactobacillus inulinus* and *Streptococcus salvarius* subsp. *Thermophilus; Bifidobacterium* species such as *Bifidobacterium adolescentis, animalis, bifidum, breve, lactis, longum* and *infantis*;

*Saccharomyces cerevisiae*; and

Bacteria such as *Bacillus* (*cereus* var *toyo* or *subtilis*), *Bacillus coagulans, B licheniformis, Escherichia coli* strain nissle and *Propionibacterium freudenreichii*.

Specific examples of probiotic microorganisms include, but are not limited to *Bifidobacterium bifidum, Bifidobacterium infantis, Bifidobacterium longum, Lactobacillus acidophilus, Lactobacillus alimentarius, Lactobacillus casei* subsp. *Casei, Lactobacillus casei Shirota, Lactobacillus paracasei, Lactobacillus curvatus, Lactobacillus delbruckii* subsp. *Lactis, Lactobacillus gasseri, Lactobacillus johnsonii, Lactobacillus reuteri, Lactobacillus rhamnosus* (*Lactobacillus* GG), *Lactobacillus sake, Lactococcus lactis, Streptococcus thermophilus, Staphylococcus carnosus* and *Staphylococcus xylosus*, and mixtures thereof.

Exemplary microorganisms may be formulated in powdered form, i.e., in a dry form, or in the form of suspensions or solutions.

If necessary, exemplary microorganisms may be formulated within compositions in an encapsulated form so as to significantly improve their survival time. In such cases, the presence of a capsule can in particular delay or prevent degradation of microorganisms in the gastrointestinal tract.

Exemplary microorganisms include probiotic microorganisms derived from the group of lactic acid bacteria, such as in particular *Lactobacillus* and/or *Bifidobacterium*. By way of illustration, exemplary lactic acid bacteria include, but are not limited to, *Lactobacillus johnsonii, Lactobacillus reuteri, Lactobacillus rhamnosus, Lactobacillus paracasei, Lactobacillus casei* or *Bifidobacterium bifidum, Bifidobacterium breve, Bifidobacterium longum, Bifidobacterium animalis, Bifidobacterium lactis, Bifidobacterium infantis, Bifidobacterium adolescentis* or *Bifidobacterium pseudocatenulatum*, and mixtures thereof.

Particularly suitable species include *Lactobacillus johnsonii, Lactobacillus paracasei, Bifidobacterium adolescentis, Bifidobacterium longum*, and *Bifidobacterium lactis* NCC 2818 [also entitled (Bb 12) (ATCC27536)] respectively deposited according to the Treaty of Budapest with the Pasteur Institute (28 rue du Docteur Roux, F-75024 Paris cedex 15) on Jun. 30, 1992, Jan. 12, 1999, Apr. 15, 1999, Apr. 15, 1999 and Jun. 7, 2005 under the following designations: CNCM I-1225, CNCM I-2116, CNCM I-2168, and CNCM I-2170 and CNCM I-3446, and the genus *Bifidobacterium longum* (BB536). The *Bifidobacterium lactis* (CNCM I-3446) strain can be obtained from Hansen (Chr. Hansen A/S, 10-12 Boege Alle, P.O. Box 407, DK-2970 Hoersholm, Denmark).

In exemplary embodiments, compositions include at least two microorganisms, in particular probiotic microorganisms, and/or metabolites and/or fractions, that are different. These microorganisms can differ in terms of their nature, for example bacterium and fungus, or else in terms of family, genus or species, or only in terms of strain.

Exemplary compositions may thus comprise at least one microorganism chosen from those mentioned above and a second microorganism that may or may not also be chosen from these microorganisms.

In exemplary embodiments, compositions may contains at least one *Lactobacillus* sp microorganism and at least one *Bifidobacterium* sp microorganism, e.g., in in equivalent amounts, in a proportion of $10^{10}$ cfu, respectively, etc.

Microorganisms and/or fractions and/or metabolites can be formulated in an appropriate carrier, for example, in an amount of at least $10^3$ cfu/g and at doses ranging, for example, from $10^5$ to $10^{15}$ cfu/g and $10^3$ to $10^{12}$ cfu/g of carrier.

Exemplary compositions, particularly compositions intended to be administered orally, may comprise, for example, for live microorganisms in amounts, for example, of from $10^3$ to $10^{15}$ cfu/g, from $10^5$ to $10^{15}$ cfu/g, and from $10^7$ to $10^{12}$ cfu/g of microorganisms per gram of carrier, or at equivalent calculated doses for inactive or dead microorganisms or for microorganism fractions or for produced metabolites. Exemplary compositions for topical application may comprise, for example, from $10^3$ to $10^{12}$ cfu/g, from $10^5$ to $10^{10}$ cfu/g, and from $10^7$ to $10^9$ cfu/g of microorganisms.

When compositions comprise metabolites, the metabolite contents in the compositions can correspond substantially to the contents that can be produced, for example, by $10^3$ to $10^{15}$ cfu, $10^5$ to $10^5$ cfu or $10^7$ and $10^{12}$ cfu of live microorganisms per gram of carrier.

In compositions that are administered orally, concentrations of microorganisms can be adjusted to correspond to doses (expressed as microorganism equivalent) ranging, for example, from $5\times10^5$ to $10^{13}$ cfu/d and $10^8$ to $10^{11}$ cfu/d.

Microorganisms can be included in exemplary compositions in a live, semi-active or inactivated, or dead form.

Microorganisms may also be included in the form of fractions of cell components or in the form of metabolites. Microorganisms, metabolites or fractions can also be introduced in the form of a lyophilized powder or of a culture supernatant and/or, where appropriate, in a concentrated form.

In topical compositions, it may be advantageous to use microorganisms in inactivated, or even dead, form.

Divalent Inorganic Cation

In exemplary embodiments, one or more divalent inorganic cations may be used.

In some such embodiments, at least two or even three different divalent inorganic cations may be used.

In exemplary embodiments, divalent inorganic cations can be used in various forms. Divalent inorganic cations can be in the form of anhydrous or hydrated inorganic or organic salt, or a chelated complex.

Exemplary salts include, but are not limited to, carbonates, bicarbonates, sulfates, glycerophosphates, chlorides, nitrates, acetates, hydroxides, oxides, α-hydroxy acid salts (citrates, tartrates, lactates, malates) or salts of fruit acids, or else amino acid salts (aspartate, arginate, fumarate) or fatty acid salts (palmitate, oleate, caseinate, behenate).

In exemplary embodiments, divalent inorganic cations may be chosen from manganese, copper and/or zinc.

In exemplary embodiments, divalent inorganic cations are alkaline earth metals. Exemplary alkaline earth metals include, but are not limited to, barium, calcium, magnesium, strontium and/or beryllium.

Advantageously, divalent inorganic cations, and in particular alkaline earth metals, employed in exemplary embodiments are in the form of salts. Exemplary salts include, but are not limited to, calcium nitrate, strontium nitrate, magnesium gluconate, calcium lactate, strontium gluconate, magnesium lactate, calcium chloride, strontium chloride, magnesium chloride, calcium carbonate, strontium sulfate, magnesium sulfate, calcium glycerophosphate, calcium citrate, magnesium citrate, strontium acetate and magnesium acetate, and mixtures thereof.

In exemplary embodiments, at least one divalent inorganic cation chosen from strontium citrate, chloride, gluconate, sulfate, lactate and/or acetate, calcium citrate, chloride, gluconate, sulphonate, lactate and/or acetate and/or magnesium citrate, chloride, gluconate, sulfate, lactate and/or acetate salts, and mixtures thereof, is used.

In exemplary methods and compositions, at least two different divalent inorganic cations, and in particular two alkaline earth metals, in the form of organic salts are used.

Divalent inorganic cations can also be used in the form of chelated complexes, in particular complexes chelated with crystalline or ionized proteins.

Divalent inorganic cations may also be in a specific form that is stored by a microorganism, for example of the yeast type, like selenium.

Cations can be introduced as they are into exemplary compositions, or by employing compounds or mixtures of compounds known to contain high concentrations of at least one cation. For example, as a source of metal salts, use may be made of extracts of plants or yeasts rich in cations. Similarly, calcium may, for example, be introduced via a milk extract.

Amounts of divalent inorganic cations content used in exemplary embodiments depend, of course, on forms of cations under consideration, and can be determined by simple, routine experimentation. Daily doses can, for example, range from 100 μg to 5 μg, 1 mg to 2 g or from 10 mg to 1.3 g.

In exemplary compositions intended for oral administration, divalent inorganic cation concentrations can be adjusted to correspond to doses ranging, for example, from 1 to 3000 mg/day or from 10 to 2000 mg/day.

Exemplary compositions and methods may include, for example, combinations of at least one magnesium and/or calcium salt, especially organic salts such as magnesium gluconate, lactate and/or citrate and/or calcium gluconate, lactate and/or citrate and/or strontium nitrate, with at least one lactic acid bacterium, such as *Lactobacillus* sp. and/or *Bifidobacterium lactis* "CNCM I-3446."

In exemplary embodiments, compositions can be administered topically or orally.

Exemplary compositions may be in any pharmaceutical form normally used for a particular route for administration.

Suitable carriers may vary widely depending on the type of composition under consideration.

Food or pharmaceutical carriers that are especially suitable include milk, yogurt, cheese, fermented milks, milk-based fermented products, ice creams, fermented cereal-based products, milk-based powders, formulas for children and infants, foods for animals, in particular pets, tablets or lozenges, liquid bacterial suspensions, oral supplements in dry form and oral supplements in liquid form.

Exemplary compositions may be food compositions for human consumption. For example, exemplary compositions may be complete nutritional foods, drinks, mineral waters, soups, dietetic supplements and replacement foods, nutritional bars, confectionery, milk-based or fermented milk-based products, yogurts, milk-based powders, enteral nutrition products, compositions for children and/or infants, cereal-based products or fermented cereal-based products, ice creams, chocolate, coffee, "culinary" products such as mayonnaise, tomato puree or salad dressings. Exemplary compositions may be formulated for animal use.

Cosmetic products may be aqueous, aqueous-alcoholic or oily solutions, dispersions of the solution type or dispersions of the lotion or serum type, emulsions having a liquid or semi-liquid consistency of the milk type, suspensions or emulsions of the cream, aqueous gel or anhydrous gel type, microemulsions, microcapsules, microparticles, or vesicular dispersions of ionic and/or non-ionic type.

A wide variety of orally-administered compositions and food supplements are contemplated. Exemplary compositions and supplements may be formulated by usual methods for producing sugar-coated tablets, gelatin capsules, gels, emulsions, tablets, capsules or solutions. Active agents can be incorporated into any other forms of food supplements or of enriched foods, for example food bars, or compacted or non-compacted powders. The powders can be diluted with water, in a fizzy drink, dairy products or soy-derived products, or can be incorporated into food bars.

Exemplary active agents can be formulated with the usual excipients and constituents for such oral compositions or food supplements, e.g., in fatty and/or aqueous constituents, humectifying agents, thickeners, preserving agents, texturing, flavouring and/or coating agents, antioxidants, preserving agents and dyes that are usual in the food art.

Formulating agents and excipients for oral compositions, and in particular for food supplements, are known in this art and are not here the subject of a detailed description.

Of course, exemplary oral compositions may contain several other active agents.

Exemplary active agents that can be used include, but are not limited to, vitamins B3, B5, B6, B8, C, E or PP, carotenoids, curcuminoids and niacin.

Exemplary methods and compositions may employ antioxidant complexes comprising vitamins C and E and at least one carotenoid, such as a carotenoid chosen from β-carotene, lycopene, astaxanthine, zeaxanthine and lutein, flavonoids such as catechins, hesperidin, proanthocyanidins and anthocyanins.

Exemplary compositions may include at least one prebiotic or a mixture of prebiotics. More particularly, prebiotics can be chosen from oligosaccharides, produced from glucose, galactose, xylose, maltose, sucrose, lactose, starch, xylan, hemicellulose, inulin, gums, of the acacia type for example, or mixtures thereof. Exemplary oligosaccharides may include at least one fructooligosaccharide. Further exemplary prebiotics may include a mixture of fructooligosaccharide and of inulin.

Exemplary cosmetic and/or dermatological compositions for topical application can be in the form of aqueous, aqueous-alcoholic or oily solutions, of dispersions of the solution type or dispersions of the lotion or serum type, of emulsions that have a liquid or semi-liquid consistency of the milk type, obtained by dispersion of a fatty phase in an aqueous phase (O/W) or vice versa (W/O), or of suspensions or emulsions that have a soft, semi-solid or solid consistency of the cream, aqueous gel or anhydrous gel type, or else of microemulsions, of microcapsules, of microparticles, or of vesicular dispersions of ionic and/or non-ionic type.

Exemplary compositions may be prepared according to usual, known methods.

Exemplary compositions include cleansing, protective, treatment or care creams for the face, for the hands, for the feet, for the major anatomical folds or for the body (for example day creams, night creams, makeup-removing creams, foundation creams, sun creams), makeup products such as fluid foundations, makeup-removing milks, protective or care milks for the body, aftersun milks, skincare lotions, gels or foams, such as cleansing or disinfecting lotions, sun lotions, artificial tanning lotions, bath compositions, deodorant compositions containing a bactericidal agent, aftershave gels or lotions, depilatory creams, or compositions for insect bites.

Exemplary compositions may also include solid preparations such as soaps or cleansing cakes.

Exemplary compositions may also be used for the hair, in the form of aqueous, alcoholic or aqueous-alcoholic solutions, or in the form of creams, gels, emulsions or mousses, or else in the form of aerosol compositions containing a pressurized propellant.

When compositions are provided as emulsions, the proportion of the fatty phase can range from 5 to 80% by weight, and preferably from 5 to 50% by weight, relative to the total weight of the composition. The oils, the emulsifiers and the coemulsifiers used in the composition in the form of an emulsion are chosen from those conventionally used in the cosmetics and/or dermatological field. The emulsifier and the coemulsifier may be present, in the composition, in a proportion ranging from 0.3 to 30% by weight, and preferably from 0.5 to 20% by weight, relative to the total weight of the composition.

When compositions are provided as oily solutions or gels, the fatty phase can represent more than 90% of the total weight of the composition.

Exemplary cosmetic and/or dermatological compositions can also contain adjuvants that are employed in the cosmetic, pharmaceutical and/or dermatological arts, such as hydrophilic or lipophilic gelling agents, hydrophilic or lipophilic active agents, preserving agents, antioxidants, solvents, fragrances, fillers, screening agents, bactericides, odour absorbers and dyestuffs. Amounts of these various adjuvants may be those conventionally used in the field under consideration, e.g., from 0.01 to 20% of the total weight of the composition. Depending on their nature, adjuvants can be introduced into a fatty phase and/or an aqueous phase.

Exemplary fats include, but are not limited to, mineral oils such as, for example, hydrogenated polyisobutene and liquid petroleum jelly, plant oils such as, for example, a liquid fraction of shea butter, sunflower oil and apricot kernel oil, animal oils such as, for example, perhydrosqualene, synthetic oils, in particular purcellin oil, isopropyl myristate and ethylhexyl palmitate, and fluoro oils such as, for example, perfluoropolyethers. Use may also be made of fatty alcohols, and fatty acids such as, for example, stearic acid and such as, for example, waxes, in particular paraffin wax, carnauba wax and beeswax. Use may also be made of silicone compounds such as silicone oils and, for example, cyclomethicone and dimethicone, and waxes, resins and gums that contain silicone. Exemplary fats may or may not be functionalized.

Exemplary emulsifiers include, but are not limited to, glyceryl stearate, polysorbate 60, a mixture of cetyl stearyl alcohol/oxyethylenated cetyl stearyl alcohol containing 33 mol of ethylene oxide sold under the name Sinnowax AO® by the company Henkel, a mixture of PEG-6/PEG-32/glycol stearate sold under the name Tefose® 63 by the company Gattefosse, PPG-3 myristyl ether, silicone emulsifiers such as cetyl dimethicone copolyol and sorbitan monostearate or tristearate, PEG-40 stearate, and oxyethylenated (20 EO) sorbitan monostearate.

Exemplary solvents include, but are not limited to, lower alcohols, in particular ethanol and isopropanol, and propylene glycol.

Exemplary hydrophilic gelling agents include, but are not limited to, carboxylic polymers such as carbomer, acrylic copolymers such as acrylate/alkyl acrylate copolymers, polyacrylamides and in particular the mixture of polyacrylamide, C13-14-isoparaffin and Laureth-7 sold under the name Sepigel 305® by the company Seppic, polysaccharides for instance cellulose derivatives such as hydroxyalkylcelluloses and in particular hydroxylpropylcellulose and hydroxyethylcellulose, natural gums such as guar, carob and xanthan gums, and clays.

Exemplary lipophilic gelling agents include, but are not limited to, modified clays such as bentones, metal salts of fatty acids such as aluminium stearates and hydrophobic silica, or else ethylcellulose and polyethylene.

Exemplary hydrophilic active agents include, but are not limited to, proteins or protein hydrolysates, amino acids, polyols, in particular $C_2$ to $C_{10}$ polyols such as glycerol, sorbitol, butylene glycol and polyethylene glycol, urea, allantoin, sugars and sugar derivatives, water-soluble vitamins, starch, and bacterial or plant extracts such as those of aloe vera.

Exemplary lipophilic active agents include, but are not limited to, retinol (vitamin A) and its derivatives, tocopherol (vitamin E) and its derivatives, ceramides and essential oils.

In exemplary compositions and methods, active agents can be combined with active agents for preventing and/or treating skin conditions.

Exemplary compositions may include a spring and/or mineral water chosen, for example, from Vittel water, water from the Vichy basin and Roche Posay water.

Exemplary methods for cosmetic treatment can be carried out by applying cosmetic and/or dermatological compositions such as described above, according to normal techniques for using such compositions. Exemplary application methods include application of creams, gels, sera, lotions, makeup-removing milks or aftersun compositions to the skin or to dry hair, application of a hair lotion to wet hair, application of shampoos, or else application of dentifrice to the gums.

Exemplary cosmetic methods may be carried out by topical administration or by oral administration, daily for example, of exemplary compositions, which may, for example, be formulated in the form of gelatin capsules, gels, lotions, sugar-coated tablets, emulsions, tablets, capsules or oral ampules, in an appropriate amount and number, according to their form, so that the active agents are administered, for example, at a rate of $5 \times 10^5$ to $10^{13}$ cfu per day or $10^6$ to $10^{11}$ cfu per day, in terms of microorganisms, or at equivalent doses of partially inactivated or dead microorganisms or of microorganism fractions or of metabolites produced.

In further exemplary embodiments, administration may be repeated until divalent inorganic cations are administered at doses, for example, of 1 to 3000 mg per day or 10 to 2000 mg per day.

Exemplary methods can include a single administration. In further embodiments, administration may be repeated, for example, 2 to 3 times daily, over a day or more, and generally over a prolonged period of at least 4 weeks, or even 4 to 15 weeks, with, where appropriate, one or more periods of interruption.

In the foregoing description and following examples, unless otherwise indicated, percentages are percentages by weight and the ranges of values written as "between . . . and . . . " and "from . . . to . . . " include the upper and lower limits specified. Components of compositions described herein are mixed, before they are formulated, in an order and under conditions that are readily determined by those skilled in the art.

This invention is illustrated by the following examples, which are merely for the purpose of illustration.

Examples of Compositions for Topical Administration

Example 1

Sensitive Skin Facial Lotion

| | |
|---|---|
| *Lactobacillus* sp. powder | 5.00 |
| Magnesium gluconate | 3.00 |
| Calcium lactate | 2.00 |
| Antioxidant | 0.05 |
| Isopropanol | 40.00 |
| Preserving agent | 0.30 |
| Water | qs 100% |

Example 2

Dry and Sensitive Skin Facial Care Milk

| | |
|---|---|
| Magnesium chloride | 3.00 |
| Calcium ascorbate | 3.00 |
| *Lactobacillus* sp. powder | 5.00 |
| Glyceryl stearate | 1.00 |
| Cetyl stearyl alcohol/oxyethylenated cetyl stearyl alcohol containing 33 mol EO (Sinnowax AO ® sold by the company Henkel) | 3.00 |
| Cetyl alcohol | 1.00 |
| Dimethicone (DC 200 Fluid ® sold by the company Dow Corning) | 1.00 |
| Liquid petroleum jelly | 6.00 |
| Isopropyl myristate (Estol IMP 1514 ® sold by Unichema) | 3.00 |
| Antioxidant | 0.05 |
| Glycerol | 20.00 |
| Preserving agent | 0.30 |
| Water | Qs 100 |

Example 3

Sensitive Skin Facial Care Gel

| | |
|---|---|
| Strontium nitrate | 4.00 |
| *Lactobacillus* sp. | 5.00 |
| Hydroxypropylcellulose (Klucel H ® sold by the company Hercules) | 1.00 |
| Vitamin E | 2.50 |
| Antioxidant | 0.05 |
| Isopropanol | 40.00 |

Example 4

Dry and Sensitive Skin Facial Care Milk

| | |
|---|---|
| Magnesium ascorbate | 3.00 |
| Blackcurrant seed oil | 4.00 |
| Borage oil | 4.00 |
| *Lactobacillus* sp. | 5.00 |
| Glyceryl stearate | 1.00 |
| Cetyl stearyl alcohol/oxyethylenated cetyl stearyl alcohol containing 33 mol EO (Sinnowax AO ® sold by the company Henkel) | 3.00 |
| Cetyl alcohol | 1.00 |
| Dimethicone (DC 200 Fluid ® sold by the company Dow Corning) | 1.00 |
| Liquid petroleum jelly | 6.00 |
| Isopropyl myristate (Estol IPM 1514 ® sold by Unichema) | 3.00 |
| Glycerol | 20.00 |
| Preserving agent | 0.30 |
| Water | Qs 100 |

Examples of Compositions for Oral Administration

Example 5

Powder Stick

| | | |
|---|---|---|
| Active principle | | |
| *Lactobacillus* sp. | $10^{10}$ | cfu |
| Magnesium citrate | 200 | mg |
| Calcium citrate | 600 | mg |
| Excipient | | |
| Xanthan gum | 0.8 | mg |
| Sodium benzoate | 0.2 | mg |
| Maltodextrin | qs 30 | g |

One stick per day can be taken.

Example 6

Powder Stick

| | | |
|---|---|---|
| Active principle | | |
| *Lactobacillus* sp. | $10^{10}$ | cfu |
| *Bifidobacterium* sp. | $10^{10}$ | cfu |
| Calcium citrate | 50 | mg |
| Excipient | | |
| Xanthan gum | 0.8 | mg |
| Sodium benzoate | 0.2 | mg |
| Maltodextrin | qs 30 | g |

One stick per day can be taken.

Example 7

Powder Stick

| | | |
|---|---|---|
| Active principle | | |
| *Lactobacillus* sp. | $10^{10}$ | cfu |
| *Bifidobacterium* sp. | $10^{10}$ | cfu |
| Magnesium citrate | 50 | mg |
| Excipient | | |
| Xanthan gum | 0.8 | mg |
| Sodium benzoate | 0.2 | mg |
| Maltodextrin | qs 30 | g |

One stick per day can be taken.

Example 8

Capsule

| | mg/capsule |
|---|---|
| *Lactobacillus* sp. | $10^8$ cfu |
| Magnesium gluconate | 150 |
| Vitamin C | 60 |
| Magnesium stearate | 0.02 |

One to three of these capsules can be taken per day.

Example 9

Capsule

| | mg/capsule |
|---|---|
| *Lactobacillus* sp. | $10^9$ cfu |
| Calcium citrate | 300 |
| Vitamin C | 60 |
| Magnesium stearate | 0.02 |

One to three capsules can be taken per day.

Example 10

Formulation of the Sugar-Coated Tablet Type

| | mg/tablet |
|---|---|
| Active materials | |
| Magnesium gluconate | 50 |
| *Lactobacillus* sp. | $5 \times 10^8$ cfu |
| Calcium citrate | 200 |
| Excipient of the core of the sugar-coated tablet | |
| Microcrystalline cellulose | 70 |
| Encompress ™ | 60 |

(-continued from previous: Preserving agent 0.30; Water qs 100%)

-continued

|  | mg/tablet |
| --- | --- |
| Magnesium stearate | 3 |
| Anhydrous colloidal silica | 1 |
| Coating agent | |
| Shellac | 5 |
| Talc | 61 |
| Sucrose | 250 |
| Polyvidone | 6 |
| Titanium dioxide | 0.3 |
| Colorant | 5 |

This type of sugar-coated tablet can be taken 1 to 3 times per day.

Example 11

Formulation of the Sugar-Coated Tablet Type

|  | mg/tablet |
| --- | --- |
| Active materials | |
| Magnesium lactate | 50 |
| *Bifidobacterium* sp. | $10^9$ cfu |
| *Lactobacillus* sp. | $10^9$ cfu |
| Calcium lactate | 200 |
| Excipient of the core of the sugar-coated tablet | |
| Microcrystalline cellulose | 70 |
| Encompress ™ | 60 |
| Magnesium stearate | 3 |
| Anhydrous colloidal silica | 1 |
| Coating agent | |
| Shellac | 5 |
| Talc | 61 |
| Sucrose | 250 |
| Polyvinylidone | 6 |
| Titanium dioxide | 0.3 |
| Colorant | 5 |

This type of sugar-coated tablet can be taken 1 to 3 times per day.

Example 12

Two oral compositions, one based only on a probiotic microorganism (B) and the other combining with this microorganism two alkaline earth metal salts (C) are tested for their effectiveness with respect to skin dryness and sensitivity, with regard to a placebo composition (A). The compositions have the following contents:

A: Maltodextrin.

B: $1 \times 10^{10}$ cfu *Lactobacillus paracasei* CNCM I-2116+1× $10^{10}$ cfu *Bifidobacterium lactis* (CNCM I-3446).

C: $1 \times 10^{10}$ cfu *Lactobacillus paracasei* CNCM I-2116+1× $10^{10}$ cfu *Bifidobacterium lactis* (CNCM I-3446)+1 g of calcium citrate+300 mg of magnesium citrate.

Treatment consists of the daily and oral administration of a single treatment unit for a period of eight weeks.

This study is carried out on 99 adult female individuals having ages between 18 and 50, who, following clinical evaluation (clinical score for dryness of the legs and roughness of the face) and self-evaluation by means of a questionnaire (validated sensitive skin questionnaire), are identified as individuals with dry and sensitive skin.

The 99 individuals are divided into three parallel groups of 33 individuals, with two groups receiving the tested products and one group receiving the placebo.

The effect of the two supplements tested is assessed by comparison with the control "placebo" formulation. The results obtained are given in Table I below.

TABLE I

| % Variation between D1 and D57 and significance versus placebo (1) | Food supplement based only on probiotics (B) | Food supplement according to the invention (C) |
| --- | --- | --- |
| Clinical score: Decrease compared with D1 Dryness of the legs | −34% | −42% (p = 0.2) |
| Self-evaluation: Decrease compared with D1 Dryness of the legs | −28% (p = 0.2) | −36% (p = 0.006) |
| Moisturization factor: Increase compared with D1 Urea | +29% (p = 0.6) | +75% (p = 0.02) |

(1) Analysis of the contrasts between D1 and D57, between the treatment groups and the placebo group.

Example 13

The oral composition of Example 10 is tested in terms of skin sensitivity is tested on the individuals considered for the study in Example 12 (evaluation of skin sensitivity by means of a lactic acid test or stinging test).

A reduction in skin sensitivity of approximately −42% (p=0.6) between D1 and D57 is observed in the treated individuals.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A cosmetic treatment method for at least one of preventing and treating at least one of sensitive skin and dry skin, comprising:

orally administering to a human a composition comprising at least an effective amount of at least one agent and at least an effective amount of at least one divalent inorganic cation;

wherein:

the at least one agent comprises at least one member selected from the group consisting of at least one microorganism, a fraction of the at least one microorganism and a metabolite of the at least one microorganism;

said at least one microorganism comprises at least one lactic acid bacterium selected from the genus *Bifidobacterium*;

said at least one microorganism further comprises at least one lactic acid bacterium selected from the genus *Lactobacillus* sp;

the at least one divalent inorganic cation comprises at least one salt selected from the group consisting of a magnesium salt and a calcium salt;

said at least one divalent inorganic cation is administered at a rate of about 1 to about 3000 mg per day; and said at least one agent is administered at a rate of about $5 \times 10^5$ to about $10^{13}$ cfu per day.

2. The cosmetic treatment method of claim 1, wherein the at least one divalent inorganic cation is in the form of a salt other than a sulfate.

3. The cosmetic treatment method of claim 1, wherein the at least one divalent inorganic cation is in the form of at least one of an anhydrous organic salt, a hydrated organic salt and a chelated complex.

4. The cosmetic treatment method of claim 1, wherein the at least one agent is formulated in a physiologically acceptable carrier in an amount equivalent to at least $10^3$ cfu/g.

5. The cosmetic treatment method of claim 1, wherein the at least one divalent inorganic cation comprises at least two different divalent inorganic cations.

6. The cosmetic treatment method of claim 5, wherein the at least one divalent inorganic cation comprises an alkaline earth metal.

7. The cosmetic treatment method of claim 6, wherein the alkaline earth metal comprises at least one member selected from the group consisting of barium, calcium, magnesium, strontium and beryllium.

8. The cosmetic treatment method of claim 1, wherein the at least one divalent inorganic cation is in the form of at least one salt selected from the group consisting of a carbonate, a bicarbonate, a gluconate, a glycerophosphate, a chloride, a nitrate, an acetate, a hydroxide, an oxide, an α-hydroxy acid salt, a salt of a fruit acid, an amino acid salt and a fatty acid salt.

9. The cosmetic treatment method of claim 8, wherein the α-hydroxy acid salt comprises at least one member selected from the group consisting of a citrate, a tartrate, a lactate and a malate.

10. The cosmetic treatment method of claim 8, wherein the amino acid salt comprises at least one member selected from the group consisting of an aspartate, an arginate and a fumarate.

11. The cosmetic treatment method of claim 8, wherein the fatty acid salt comprises at least one member selected from the group consisting of a palmitate, an oleate, a caseinate and a behenate.

12. The cosmetic treatment method of claim 1, wherein the at least one divalent inorganic cation is in the form of at least one salt selected from the group consisting of a calcium gluconate, a calcium citrate, a calcium lactate, a calcium chloride, a calcium acetate, a magnesium gluconate, a magnesium citrate, a magnesium lactate, a magnesium chloride and a magnesium acetate.

13. The cosmetic treatment method of claim 1, wherein the composition is in the form of a cosmetic composition.

14. The cosmetic treatment method of claim 1, wherein said at least one microorganism comprises *Bifidobacterium adolescentis* (CNCM I-2168).

15. The cosmetic treatment method of claim 1, wherein said at least one microorganism comprises *Bifidobacterium longum* (CNCM I-2170).

16. The cosmetic treatment method of claim 1, wherein said at least one microorganism comprises *Bifidobacterium lactis* (CNCM I-3446).

17. The cosmetic treatment method of claim 1, wherein said at least one microorganism comprises *Bifidobacterium longum* (BB536).

18. A cosmetic treatment method for at least one of preventing and treating at least one of sensitive skin and dry skin, comprising:

at least one of orally and topically administering to a human a composition comprising at least an effective amount of at least one agent and at least an effective amount of at least one divalent inorganic cation;

wherein:

the at least one agent comprises at least one member selected from the group consisting of at least one microorganism, a fraction of the at least one microorganism and a metabolite of the at least one microorganism;

said at least one agent is administered at a rate of about $5 \times 10^5$ to about $10^{13}$ cfu per day;

the at least one divalent inorganic cation is in the form of a salt other than a sulfate;

the at least one divalent inorganic cation comprises at least one salt selected from the group consisting of a magnesium salt and a calcium salt;

said at least one divalent inorganic cation is administered at a rate of about 1 to about 3000 mg per day;

said at least one microorganism comprises at least one lactic acid bacterium selected from the genus *Bifidobacterium*; and said at least one microrganism further comprises at least one lactic acid bacterium selected from the genus *Lactobacillus* sp.

19. The cosmetic treatment method of claim 18, wherein the orally administered composition is in a form of a food composition.

20. The cosmetic treatment method of claim 18, wherein said at least one microorganism comprises *Bifidobacterium adolescentis* (CNCM I-2168).

21. The cosmetic treatment method of claim 18, wherein said at least one microorganism comprises *Bifidobacterium longum* (CNCM I-2170).

22. The cosmetic treatment method of claim 18, wherein said at least one microorganism comprises *Bifidobacterium lactis* (CNCM I-3446).

23. The cosmetic treatment method of claim 18, wherein said at least one microorganism comprises *Bifidobacterium longum* (BB536).

* * * * *